United States Patent [19]

Haard et al.

[11] Patent Number: 4,690,826

[45] Date of Patent: Sep. 1, 1987

[54] BACTERIAL ENZYME USED AS CHEESE RIPENING AID

[75] Inventors: Norman F. Haard, Outer Cove; Thakor R. Patel, St. Johns, both of Canada

[73] Assignee: Canadian Patents and Development Limited, Ottawa, Canada

[21] Appl. No.: 863,443

[22] Filed: May 15, 1986

[51] Int. Cl.<sup>4</sup> ............................................. A23C 19/02
[52] U.S. Cl. ........................................ 426/36; 426/40; 426/43; 435/876
[58] Field of Search ....................... 426/34, 35, 36, 37, 426/38, 39, 40, 42, 43, 56, 580, 582; 435/822, 874, 876

[56] References Cited

U.S. PATENT DOCUMENTS

| | | | |
|---|---|---|---|
| 3,151,039 | 9/1964 | Arima et al. | 195/62 |
| 3,482,997 | 12/1969 | Murray et al. | 426/36 |
| 3,689,286 | 9/1972 | Luksas | 99/115 |
| 3,875,305 | 4/1975 | Storrs | 426/38 |
| 4,062,730 | 12/1977 | Malkki et al. | 195/62 |
| 4,158,607 | 6/1979 | Kalinowski et al. | 195/62 |

FOREIGN PATENT DOCUMENTS 2422005  5/1975  Fed. Rep. of Germany ........ 426/36

OTHER PUBLICATIONS

Scientific American–"Cheese", pp. 88–99.
Reprint J. Food. Sci., 50(3), pp. 602–604 & 609, 1985.

Primary Examiner—Raymond N. Jones
Assistant Examiner—Marianne M. Cintins

[57] ABSTRACT

A process for producing cheddar cheese having accelerated ripening properties. The process involves using a ripening aid which is a protease derived from the psychrotrophic flora of raw milk, and preferably from the bacteria *Pseudomonas fluorescens*. The ripening aid is added to the milk starting material prior to or simultaneously with the treatment with a coagulant (renneting agent) and it remains in the cheese product and enhances the development of desirable flavor during the aging (ripening) of the cheese.

15 Claims, 1 Drawing Figure

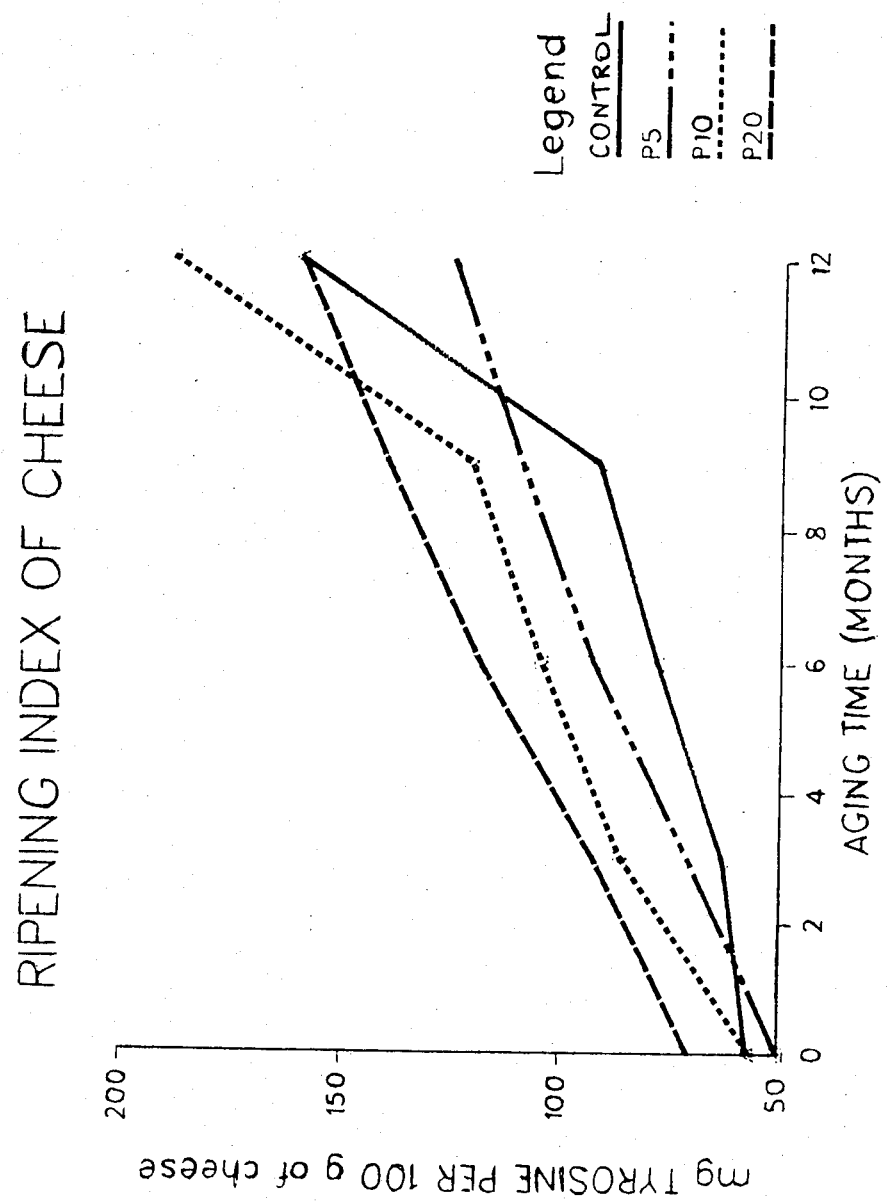

BACTERIAL ENZYME USED AS CHEESE RIPENING AID

BACKGROUND OF THE INVENTION

I. Field of the Invention

This invention relates to processes for making cheese and to cheese products so made. More particularly, the invention relates to the use of ripening aids employed in processes for making Cheddar cheese.

II. Description of the Prior Art

The manufacture of Cheddar cheese is carried out on a large scale in many countries. Very briefly summarized, the traditional manufacturing process involves coagulating milk to form solid curds and liquid whey, separating the curds from the whey, treating the curds to form a Cheddar cheese product and aging (i.e. so-called "ripening") the cheese product under controlled temperature conditions to allow the desired taste and texture to develop. If the aging or ripening period is short, the product is known as "mild" Cheddar. Longer aging periods lead to the production of "medium", "old" and "very old" Cheddars. The longer the aging period, the more the "sharp" or "tangy" taste develops, and the more valuable is the resulting cheese. A more complete description of cheese making in general, and Cheddar cheese making in particular, can be found in an article by Frank V. Kosikowski published in the Scientific American, Vol. 252(5), 1985, pp. 88 to 99. The disclosure of this article is incorporated herein by reference.

The production of Cheddar cheese in large quantities has recently encountered several problems. Firstly, while the "old" and "very old" Cheddars command a higher price in the marketplace, they are expensive to produce because of the storage and refrigeration costs required for the lengthy ripening process, which can involve up to three years of storage at a temperature of about 10° C.

Furthermore, the coagulant traditionally employed for coagulating the milk is "calf rennet", i.e. an enzyme extract from the stomachs of young, milk-fed calves. Because of a recent reduction in the number of calves being slaughtered and an increased demand for cheese, calf rennet has increased significantly in price in recent years. Alternative coagulants, i.e. so-called rennet substitutes, are known and used on a large scale, e.g. porcine pepsin, bovine pepsin and *Mucor miehei* protease, but they do not facilitate the ripening process in Cheddar cheese manufacture as effectively as calf rennet. As a result, they are commonly employed only for the production of mild Cheddar cheese. Taking porcine pepsin as an example, this rennet substitute is unstable at the pH values and temperatures employed during the "cheddaring" step of the process and, as a result, the Cheddar ages very slowly compared to Cheddar prepared with calf rennet.

A further problem encountered by Cheddar cheese producers is that the use of raw (unpasteurized) milk is discouraged or banned by many regulatory agencies because of the risk that pathogenic bacteria in the raw milk may contaminate the cheese product. However, the use of pasteurized or partially pasteurized milk as the starting material has an effect on the ripening process because certain bacteria present in raw milk apparently affect the process of flavour development. Thus, longer ripening periods are required than when raw milk is employed.

The ripening period cannot be reduced by increasing the temperature at which the product is stored because of possible flavour defects and because of the accompanying risk of spoilage of the cheese. Accordingly, attempts have been made to provide cheese ripening aids, i.e. materials that can be added to the milk starting material or to the cheese product to decrease the ripening period without adversely affecting the flavour and texture of the cheese. A limited number of products are available commercially as cheese ripening aids, e.g. β-galactosidase (sold by G. B. Fermentations under the trade mark Maxilact), and there are reports of accelerated ripening by the use of microbial proteases, e.g. *B. subtilis* neutral protease, *Aspergillis orryzae* acid protease, *B. licheniformis* alkaline protease, and *K. lactis* proteases, and by the use of *Streptococcus lactis* mutants and microbial lipases. However, commerical proteases having a high ratio of endo- to exo-peptidase activity tend to cause excessively gross proteolysis leading to abnormal body/texture development and some cause a bitter off-flavour in the aged cheese. The efficacy of β-galactosidase as an accelerator of cheese ripening has, moreover, been questioned in the scientific literature (Advances in the Microbiology and Biochemistry of Cheese and Fermented Milk, by B. A. Law, 1984, Elsevier Applied Science, p. 218).

There is accordingly a need for a more effective cheese ripening aid for use in the manufacture of Cheddar cheese.

SUMMARY OF THE INVENTION

An object of the present invention is to provide an effective ripening aid for use in the manufacture of Cheddar cheese.

Another object of the present invention is to provide a process for producing Cheddar cheese employing an improved ripening aid.

A further object of the present invention is to provide a Cheddar cheese having a reduced ripening period resulting from the use of an improved ripening aid.

The present invention is based on the finding that psychrotrophic flora present in raw milk produce proteases (proteolytic enzymes) which are effective as cheese ripening aids. Addition of these proteases to pasteurized milk prior to or simultaneously with the addition of a coagulant (renneting agent e.g. calf rennet or porcine pepsin) and preparation of the cheese by the conventional method results in a product which matures faster than cheeses containing no such protease.

BRIEF DESCRIPTION OF THE DRAWING

The accompanying FIGURE is a graph showing the results of a test carried out in the Example set forth below.

DETAILED DESCRIPTION OF THE INVENTION

The preferred psychrotrophic flora obtained from raw milk, i.e. those producing the most effective proteases for use as cheese ripening aids, are bacteria belonging to the species *Pseudomonas fluorescens*. These bacteria are already well known and are commonly associated with food spoilage (eggs, cured meats, fish and milk). These bacteria have been extensively discussed in articles entitled "Extracellular Heat-Resistant Proteases of Psychrotrophic Pseudomonads" by Patel, Bartlett and Hamid, 1983, J. Food. Protect. 46:90, and "Heat Stable Proteases from Psychrotrophic Pseudomonads: Comparison of Immunological Properties", by Patel, Jackman and Bartlett, 1983, Appl. Environ. Micro. 46: 6–12; the disclosures of which are incorporated herein by reference.

The proteases produced by the bacteria can be obtained by culturing the bacteria at 25° C. for about 4–5 days in a suitable liquid medium containing a nutrient such as milk or milk powder, followed by centrifuging at high speed, e.g. 10,000 rpm for about 10–15 minutes. The protease thus obtained can then be partially purified e.g. by dialysis (e.g. in Tris-HCl buffer at pH 7.2) and filtration. This procedure is described in more detail in the Patel et. al. articles referred to above.

The purfication and/or separation of the protease from the culture solution may alternatively be carried out by other conventional procedures such as precipitation, filtration, chromatography, etc.

A particularly preferred protease for use in the present invention is that obtained from the bacterial strain *Pseudomonas fluorescens* (T25). This strain can be identified on the basis of its growth at 4° C., failure to grow at 41° C., utilization of trehalose and β-alanine, positive test for catalase and oxidase, gram negative test, and its rod-like, polar flagellated structure. This microorganism and the protease are described in more detail in the above Patel et. al. articles.

It seems that the enzyme derived from the T25 strain is especially effective because this enzyme has a high proteolytic activity compared with protease samples obtained from other strains of *Ps. fluorescens*.

A sample of the T25 strain is on deposit at the Department of Biochemistry, Memorial University of Newfoundland, Faculty of Science, St. John's, Newfoundland, Canada, A1B 3X9, where the strain is identified as *Pseudomonas fluorescens* T25.

In general terms, the protease can be obtained as follows. Liquid cultures, grown in trypticase broth containing 1–2% milk powder for 4 days at 25° C., produce a protease which can be recovered from the liquid culture by centrifugation at 10,000 rpm for about 10 minutes. The protease can then be partially purified by dialysis and filtration. The heat stable protease thus obtained has a molecular weight of about 41,500.

In the present invention, the protease obtained as above can be added to raw, pasteurized or partially pasteurized milk used for cheese making. The amounts employed are preferably in the range of 5–20 mg/L, although more or less can be used, if desired. The protease has no direct effect on the growth of starter cultures normally employed in cheese making and can be added to the milk either before or after the addition of such starter cultures and either before or simultaneously with the addition of the rennetting agent. The manufacture of Cheddar cheese can then be carried out entirely in the conventional way to give a Cheddar cheese product which ripens more quickly than conventional Cheddar cheese.

While the presence of *Ps. fluorescens* bacteria and proteases derived therefrom in milk products normally results in spoilage, it is unexpectedly found that the presence of the protease accelerates the cheese ripening process without producing a spoiled flavour or texture. This may be because the conditions under which ripening takes place are not the optimum conditions for the enzyme, so that limited enzymatic activity takes place, i.e. enough for flavour enhancement but not enough for spoilage.

The ripening aid of the present invention can be used in conjunction with calf rennet or any rennet substitute. Use in conjunction with rennet substitutes of microbiological origin, rather than animal origin, is possible but less preferred. The best results are obtained when the ripening aid is used in conjunction with calf rennet or porcine pepsin.

A preferred form of the present invention is illustrated in more detail by the following Example, but the present invention should not be construed as limited thereto.

EXAMPLE 1

This Example illustrates a process of Cheddar cheese making employing porcine pepsin as the coagulant and protease extract of *Ps. fluorescens* (T25) as a ripening aid.

Four batches of cheese were made using 8 liters of pasteurized milk in each case and the following ripening aids:

1. Control (no ripening aid used)
2. T25 protease extract in the amount of 5 mg/L
3. T25 protease extract in the amount of 10 mg/L
4. T25 protease extract in the amount of 20 mg/L.

The batches of cheese were then aged and sampled at various times and the samples were rated for flavour by a test panel and compared with a commercial product.

The experimental details are given as follows:

A. ENZYME PREPARATION

Liquid cultures (250 ml) of T25, previously identified as *Pseudomonas fluorescens*, an isolate from raw milk, were grown in trypticase soy broth (TSB) supplemented with 1–2% fat-free milk powder. The growth and method of preparation of the crude extract were as described previously (Patel et al 1983 article in J. Food. Protect. referred to above). The flask was incubated at 25° C. for 4–5 days in a shaker (Psychrotherm, New Brunswick Scientific Co., New Brunswick, N.J.). Cells were removed by centrifugation at 10,000 rpm for 15 minutes. The supernatant was decanted and dialyzed in 20 mM Tris HCl buffer, pH 7.2. This dialyzed extract formed the source of the protease.

B. ENZYME ACTIVITY

The protease activity was determined by modified Hull's method (as explained in the Patel et. al. article in Appl. Environ. Micro. identified above). One enzyme unit (EU) is the amount of extract that releases 1 μmole of tyrosine equivalent per min. per mL at 25° C. The specific activity is the number of enzyme units per mg of protein.

The characteristics of the enzyme were as follows:
Enzyme Unit (EU)=1.02 mL
Protein=6.7 mg/ml
Specific Activity=0.152

C. MANUFACTURE OF CHEESE BATCHES

Raw milk samples were purchased from a local dairy and pasteurized at 63° C. for 30 minutes. Four batches of 8 L were used, i.e. a control and three samples of different concentrations of Pseudomonas protease, as indicated above.

The method of Kosikowski was used in the preparation of the cheese (Kosikowski, F., "Cheese and Fermented Milk Foods" 2nd ed., F. Kosikowski & Associates Publishers, Brooktondale, N.Y., pp. 228-236, the disclosure of which is incorporated herein by reference). A commercial starter culture, containing a mixture of *Streptococcus lactis* and *S. cremoris* was used to inoculate the pasteurized milk (40 g/8 L). Once a pH drop of 0.03-0.05 was noted, the rennetting agent, porcine pepsin (28 mg/L milk) was added, and the milk left at room temperature for 20-30 minutes until firm curd formation was obtained. The curd was then cut and the temperature raised slowly to 38-39° C., where it was maintained for approximately two hours, until the pH of the curd was 6.0. Cheddaring of the curd (drained) was done at the same temperature for another 1.5 hours (curd pH 5.3-5.4). The curd was cut (1 cm cubes), salted (2.3 g/100 g curd) and then pressed for 24 hours at 15 lb./sq. inch pressure. The pressed cheese was then vacuum packaged and stored at 5°-7° C. for ripening.

D. RIPENING AND SAMPLING OF CHEESE

Initially and every 3 months for the next year, samples from each of these four cheeses were taken and analyzed for free and total amino acid composition, ripening index (as indicated by liberated tyrosine concentration) and, as well, subjected to qualitative analysis by a trained taste panel. The amino acid compositions were determined using a Beckman Model 121 MB Amino Acid Analyser, (Biochemistry Dept., Memorial University of Newfoundland, Canada). Ripening index evaluation was carried out using the method of Vakaleris & Price (Vakeleris, D. G. and Price M. V. (1959), "A Rapid Spectrophotometric Method for Measuring Cheese Ripening", J. Dairy Sci. 42: 264-276, the disclosure of which is incorporated herein by reference). Taste panel members, initially trained in the evaluation of cheese aging, were asked to compare the four samples with commercially made cheeses and rate them according to their Cheddar taste. Statistical analyses were carried out on the results to ensure validity of the panel.

The results of the ripening index evaluations are given in Table 1 below, and the total liberated soluble tyrosine values are shown in the attached FIGURE.

TABLE 1

| | Ripening Index as indicated by total soluble tyrosine liberated | | | | |
|---|---|---|---|---|---|
| | Aging (months) | | | | |
| cheese sample ↓ | 0 | 3 | 6 | 9 | 12 |
| | conc [mg/100 g cheese] | | | | |
| (1) control | 57.08 | 63.06 | 78.16 | 91.64 | 159.5 |
| | | [10.5%] | [23.9%] | [17.2%] | [74.1%] |
| (2) T25 5 mg/L | 50.28 | 70.94 | 92.45 | 109.21 | 125.0 |
| | | [41.1%] | [30.3%] | [18.1%] | [14.5%] |
| (3) T25 10 mg/L | 56.63 | 86.07 | 104.23 | 120.55 | 188.5 |
| | | [51.0%] | [21.1%] | [15.7%] | [56.4%] |
| (4) T25 20 mg/L | 70.67 | 92.41 | 118.37 | 139.55 | 159.5 |
| | | [30.8%] | [28.1%] | [17.9%] | [14.3%] |

In the above Table, the numbers in square brackets indicate the percentage increases in the ripening index, e.g. for the control sample:

$$63.06 - 57.08 = 5.98 \div 57.08 \times 100 = 10.5\%$$

According to Vakeleris and Price: there is a trend in the relation between the age of cheese and the soluble tyrosine in the cheese extract. Soluble tyrosine tends to increase more rapidly in the early stages of ripening.

In general there was a more rapid percent increase in soluble tyrosine during the first three months of aging, followed by a steady decline. However, note the sharp increase in both the control and the T25 10 mg/L extracts at the 12 month period. Notice, also that the three samples with added T25 protease almost consistently showed higher tyrosine levels than the control, in effect connobonating results of their effect in promoting cheddaring.

The results of the evaluation of the cheeses made by the panel of experts are given in Table 2 below.

TABLE 2

Sensory Evaluation of Cheddar Cheese made with Porcine Pepsin + Added T25 Protease

| Cheddar Flavor Intensity Rank | Sample | Process | Aging (10° C.) |
|---|---|---|---|
| 1 a,b | KRAFT* (medium) | conventional | 6-12 mths. |
| 2 a,b | Porcine Pepsin | conventional | 3 mths. |
| 3 c | PP + T25 10 mg/L | conventional | 3 mths. |
| 4 d,e | PP + T25 5 mg/L | conventional | 3 mths. |
| 5 d,e | PP + T25 20 mg/L | conventional | 3 mths. |
| 1 a,b | PP + T25 10 mg/L | conventional | 6 mths. |
| 2 a,b | PP + T25 20 mg/L | conventional | 6 mths. |
| 3 c,d | PP + T25 5 mg/L | conventional | 6 mths. |
| 4 c,d | KRAFT* (medium) | conventional | 6-12 mths. |
| 5 e | Porcine pepsin | conventional | 6 mths. |
| 1 a,b | PP + T25 20 mg/L | conventional | 9 mths. |
| 2 a,b | PP + T25 10 mg/L | conventional | 9 mths. |
| 3 c,d | PP + T25 5 mg/L | conventional | 9 mths. |
| 4 c,d | KRAFT* (medium) | conventional | 6-12 mths. |
| 5 e | Porcine Pepsin | conventional | 9 mths. |
| 1 a,b | PP + T25 20 mg/L | conventional | 12 mths. |
| 2 a,b | PP + T25 10 mg/L | conventional | 12 mths. |
| 3 c,d | PP + T25 5 mg/L | conventional | 12 mths. |
| 4 c,d | KRAFT* (medium) | conventional | 6-12 mths. |
| 5 e | Porcine Pepsin | conventional | 12 mths. |

*Trade Mark

In the above Table, numbers 1 through 5 represent ranking, 1 being the highest and 5 the lowest intensity of the Cheddar flavor. The lower case letters represent the statistical significance at 5% level. Those carrying the same letters are statistically not significant at this level. For example 1 a,b and 2 a,b are statistically insignificant in their Cheddar flavor intensities (in other words they are similar) while 2 a,b and 4 d,e are statistically significant, i.e. they are dissimilar in their Cheddar flavor.

Comparison can be made between samples within a group using these lower case letters. For example 2 a,b and 4 d,e from group one (3 months) may be compared with each other but 2 a,b from this group (3 months) may not be compared to 2 a,b from the second group (6 months).

The method employed in the statistical analysis was from a Publication (No. 1637) of the Canadian Department of Agriculture, Research. Branch. "Laboratory Methods for Sensory Evaluation of Foods", by Elizabeth Larmond, Food Research Institute, Ottawa. (ISBN: 0-662-01271-2). Reprinted in 1982.

The results from taste panels conducted over a 1 year period from the manufacture of cheese using porcine pepsin plus T25 protease showed a definite effect of said protease on increased Cheddar flavor over a much shorter period of time.

T25 protease, a neutral metalloprotease with optimum pH 7.4, had limited activity at the lower pH of aging cheese, but this reduced activity was enough to cause more intense flavor among the 3 sample cheeses. This reduced activity also prevented extreme proteolysis resulting in release of peptides causing bitterness.

Taste panel members continuously rated these three sample cheeses as having a more intense Cheddar flavor than either the control (without protease) or a commercially prepared cheese of similar age.

We claim:

1. In a process for preparing Cheddar cheese which comprises treating a milk starting material with a coagulant to cause the milk starting material to form into solid curds and liquid whey, separating the solid curds from the liquid whey and treating said curds to form a Cheddar cheese product, and ripening said cheese product by allowing the product to age at a controlled temperature, the improvement which comprises adding a protease derived from bacteria of the species *Pseudomonas fluorescens* to said milk starting material in an amount of at least about 5 mg/L as a ripening aid prior to the formation of said solid curds.

2. A process according to claim 1, wherein said protease is obtained by culturing *Pseudomonas fluorescens* in a nutrient liquid for a plurality of days, centrifuging the resulting product at a speed sufficient and for a period of time sufficient to form a supernatant, removing the supernatant and separating the protease contained therein.

3. A process according to claim 1, which comprises employing a protease derived from the bacterial strain *Ps. fluorescens* T25 as said protease.

4. A process according to claim 3 wherein said protease is a crude lyophilized extract of the bacteria having the following characteristics:
Enzyme Unit (EU)=1.02 ml/ml
Protein=6.7 mg/ml
Specific Activity=0.152.

5. A process according to claim 2 wherein said enzyme has a molecular weight of about 41,500.

6. A process according to claim 3 wherein the protease is added to the milk starting material in an amount falling within the range of 5 to 20 mg/L.

7. A process according to claim 1 which comprises employing a renneting agent of animal origin as said coagulant.

8. A process according to claim 7 wherein the renneting agent is calf rennet.

9. A process according to claim 7 wherein the renneting agent is porcine pepsin.

10. A process according to claim 1 which comprises employing pasteurized milk as said milk starting material.

11. A process according to claim 1 which comprises employing partially pasteurized milk as said milk starting material.

12. A process according to claim 1 which comprises employing raw milk as said milk starting material.

13. A process according to claim 1 wherein said protease is added to said milk starting material before said coagulant is added.

14. A process according to claim 1 which comprises adding a starter culture to said milk starting material before adding said coaugulant.

15. A process according to claim 1 wherein said ripening of said cheese product is carried out for a time sufficient for said product to develop a desired Cheddar flavour.

* * * * *